US00PP11825P2

(12) United States Plant Patent
Heffner

(10) Patent No.: US PP11,825 P2
(45) Date of Patent: Mar. 27, 2001

(54) VARIETY OF PETUNIA NAMED 'TRUMPET NEON ROSE'

(75) Inventor: Mike Heffner, Lompoc, CA (US)

(73) Assignee: John Bodger and Sons Company, South El Monte, CA (US)

( * ) Notice: Subject to any disclaimer, the term of this patent is extended or adjusted under 35 U.S.C. 154(b) by 0 days.

(21) Appl. No.: 09/169,699

(22) Filed: Oct. 9, 1998

(51) Int. Cl.[7] ..... A01H 5/00

(52) U.S. Cl. ..... Plt./356

(58) Field of Search ..... Plt./356

(56) References Cited

U.S. PATENT DOCUMENTS

P.P. 9,557 * 5/1996 Suzuki et al. ..... Plt./356

* cited by examiner

*Primary Examiner*—Bruce R. Campbell
*Assistant Examiner*—Wendy A Baker
(74) *Attorney, Agent, or Firm*—Fulwider Patton Lee & Utecht, LLP

(57) ABSTRACT

The claimed cultivar brings a new color to the Trumpet series of Petunias and is characterized by a large purple rose colored flower accented in its center with a large and distinctive yellow-white circular center, over medium green foliage. As with all Trumpet Petunias, this cultivar exhibits early flowering with superior branching so that the plant may also be used in a hanging pot.

1 Drawing Sheet

BACKGROUND OF THE NEW PLANT

The present invention relates to a new and distinct variety of Petunia known by the name 'Trumpet Neon Rose' (Bodger No. 7P3389-3). The new variety was discovered in a selective breeding program by Mike Heffner at Bodger Seeds, Ltd., Lompoc, Calif. The new variety is a selection from the crossing of inventor's proprietary Petunia selection Bodger No. 7P700-5 (unpatented) which is a seedling with spreading decumbent habit and small rose colored flowers, with inventor's proprietary Petunia selection Bodger No. 7P1107-4 (unpatented) which is a seedling with upright habit and large salmon colored flowers.

This new variety is a result of a breeding program whose objective was to develop new vegetatively propagated petunias with a spreading cascading habit, large flowers and with a color range no presently available as a cutting product. The variety originated from a cross between two proprietary seedling selections taken from the existing breeding program. The progeny from this cross was grown out during the summer of 1997 and a number of single plants were selected as possible new varieties and propagated vegetatively. The cuttings were trialed and evaluated during winter and summer of 1998 at which time it was determined that this particular line, established from one single plant, was distinguishable and unique.

The new cultivar was first asexually reproduced by terminal vegetative cuttings at Bodger Seeds, Ltd., Lompoc, Calif. and has been repeatedly asexually reproduced by cuttings at Bodger Seeds, Ltd., at Lompoc Calif. It has been found to be stable and true to type through successive propagations.

The new cultivar was grown in a glass greenhouse in Lompoc, Calif., using full light, 60° Fahrenheit night temperature, 77° Fahrenheit day temperature, and grown in soil having a temperature of 80° Fahrenheit. The claimed plant was grown from a terminal vegetative cutting, and exhibited an eight to ten weeks response time from an unrooted cutting to a 25 cm flowering plant.

DESCRIPTION OF THE DRAWING

The accompanying drawing illustrates the new cultivar, the color being as nearly true as possible with color illustrations of this type.

DESCRIPTION OF THE NEW PLANT

The following detailed description sets forth characteristics of the new cultivar. The data which defines each characteristic was collected from asexual reproductions carried out by Bodger Seeds, Ltd., in Lompoc, Calif. The plant histories were taken on rooted cuttings believed to have been potted in a 25 cm pot, under full light in the greenhouse, and color readings were taken in day light using The Royal Horticultural Society of London Colour Chart.

THE PLANT

Classification:
- *Botanical.*—*Petunia×hybrida Hort.*
- *Commercial.*—'Trumpet Neon Rose' petunia.

Form: Indeterminate with moderate branching and spreading and decumbent habit. When planted in a hanging pot the stems hang down.
- *Height.*—25 cm above the top of the pot.
- *Spreading area of plant.*—116 cm in diameter.

Leaves: Leaves are simple, opposite; pinnate venation; leaves horizontal to stem.
- *Size.*— 8.1 cm length when fully expanded. 5.4 cm width when fully expanded. 1.5 mm thickness.
- *Shape.*—Elliptic.
- *Margin.*—Entire.
- *Texture.*—Sparsely pubescent.
- *Color.*—Upper: Green (R.H.S. 137A-Green Group). Lower: Green (R.H.S. 146B-Yellow-Green Group).
- *Apex.*—Broadly acute.
- *Base.*—Attenuate.

Stem:
- *General.*—Hanging; Spreading to a length of 58 cm.

*Color.*—Green (R.H.S. 144B — Yellow — Green Group).
*Internode length.*—3.5 cm.
*Diameter.*—0.3 cm.
*Anthocyanin pigmentation.*—Absent.
*Texture.*—Pubescent.

INFLORESCENCE

Young flower:
*Diameter.*—5.9 cm.
*Length.*—5.6 cm.
*Color.*—Inside: Purple (R.H.S. 74A — Red — Purple Group), with a distinctive circular are in center of Yellow-White (R.H.S. 160D — Greyed-Yellow Group), center circular area 1.6 cm in diameter. Outside: Purple Rose (R.H.S. 74C — Red — Purple Group) with faint veins in Green (R.H.S. 151B — Yellow — Green Group), with a distinctive change in coloration to Off White (R.H.S. 155B — Greyed Colors Group) with faint veins in Green (R.H.S. 151B — Yellow — Green Group) as one moves towards the base of the flower.

Mature flower:
*Diameter.*—8.3 cm.
*Length.*—6.4 cm.
*Color.*—Inside: Purple Rose (R.H.S. 74A — Red — Purple Group), with a distinctive circular area in center of Yellow—White (R.H.S. 160D — Greyed — Yellow Group), center circular area 1.6 cm in diameter. Outside: Purple Rose (R.H.S. 74C — Red — Purple Group) with faint veins in Green (R.H.S. 151B — Yellow — Green Group), with a distinctive change in coloration to Off White (R.H.S. 155B — Greyed Colors Group) with faint veins in Green (R.H.S. 151B — Yellow — Green Group) as one moves towards the base of the flower.

Open florets:
*Form.*—Single funnelform flowers; calyx five parted, petals united into flower tube; petal apex rounded to broadly acuminate.
*Texture and appearance.*—Smooth on inside, pubescent on outside, presenting large rose flowers. Approximately 150–200 open blooms per mature 25 cm pot. Flowers open above foliage and face outwards. Variety shows normal fertility and seed set. Flowers have no fragrance.

Pedicel:
*Length.*—2.6 cm.
*Thickness.*—0.3 cm.
*Texture.*—Pubescent.

Sepals:
*Quantity.*—5.
*Length.*—2.2 cm.
*Width.*—0.9 cm.
*Shape.*—Elliptic.
*Color.*—Inside: Green (R.H.S. 137A — Green Group). Outside: Green (R.H.S. 137C — Green Group).
*Apex.*—Obtuse.
*Margin.*—Entire.
*Texture.*—Pubescent.

Persistence:
*Disease resistance.*—No special disease resistance.

REPRODUCTIVE ORGANS

Stamens:
*Number.*—5 normal stamens.
*Anther.*—Level or slightly above stigma; Yellow-White.
*Filaments.*—White.

Pistils:
*Number.*—1 normal.
*Stigma.*—Green.
*Style.*—Yellow-Green.

Ovaries: Superior.

GENERAL CHARACTERISTICS

'Trumpet Neon Rose' brings a new and distinct color to the Trumpet Series of Petunias which is a group of varieties that are early flowering and very floriferous having large blooms over a medium green foliage. 'Trumpet Neon Rose' presents a large purple rose colored flower accented with a distincive yellow-white circular center.

I claim:

1. A new and distinct variety of Petunia plant, substantially as shown and described.

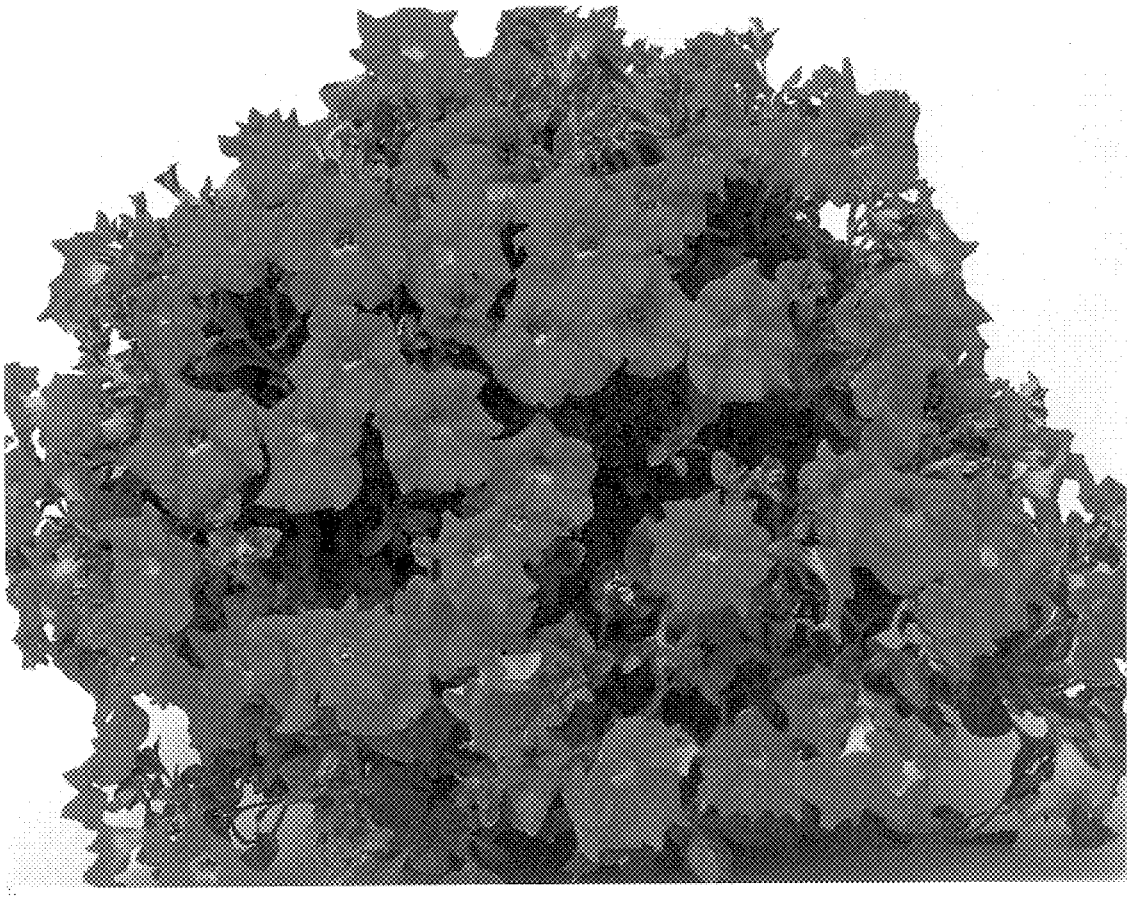

* * * * *